United States Patent
More et al.

(10) Patent No.: US 7,446,234 B2
(45) Date of Patent: Nov. 4, 2008

(54) BISPHENOL COMPOUND AND PROCESS FOR PREPARATION THEREOF

(75) Inventors: Arvind Sudhakar More, Maharashtra (IN); Prakash Purushottam Wadgaonkar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/528,490

(22) Filed: Sep. 27, 2006

(65) Prior Publication Data
US 2007/0073090 A1    Mar. 29, 2007

(30) Foreign Application Priority Data
Sep. 27, 2005    (IN) .................. 2000/DEL/2005

(51) Int. Cl.
*C07C 39/12*    (2006.01)
(52) U.S. Cl. ..................................... 568/718
(58) Field of Classification Search .............. 568/718
See application file for complete search history.

(56) References Cited
U.S. PATENT DOCUMENTS
2005/0040390 A1*    2/2005    Pfeiffer et al. ................. 257/40
* cited by examiner

*Primary Examiner*—Shaojia Anna Jiang
*Assistant Examiner*—Jennifer Y Cho
(74) *Attorney, Agent, or Firm*—Ladas & Parry LLP

(57) ABSTRACT

The present invention provides a novel bisphenol compound of formula (I).

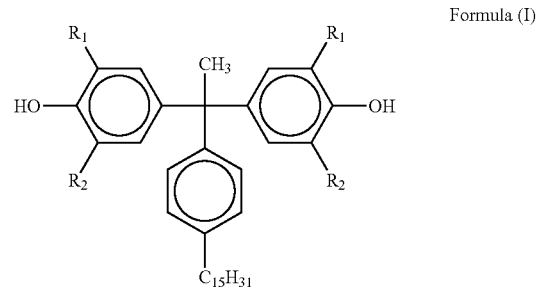

Formula (I)

wherein $R_1$ and $R_2$ are the same or different and are independently either hydrogen or methyl at each occurrence. The present invention also provides a process for preparation of these bisphenol compounds starting from Cashew Nut Shell Liquid (CNSL); —a renewable resource material. The bisphenols prepared in the present invention can be utilized as difunctional monomers for the preparation of various polymers such as epoxy resins, polyesters, polyethersulfones, polyetherketones, polyetherimides, polyarylates, polycarbonates, etc.

1 Claim, No Drawings

BISPHENOL COMPOUND AND PROCESS FOR PREPARATION THEREOF

FIELD OF THE INVENTION

The present invention provides a novel bisphenol compound. The present invention also provides a process for preparation of novel bisphenol compounds. More particularly the present invention provides a novel bisphenol compound of Formula I, where $R_1$ and $R_2$ are the same or different and independently, are either hydrogen or methyl at each occurrence.

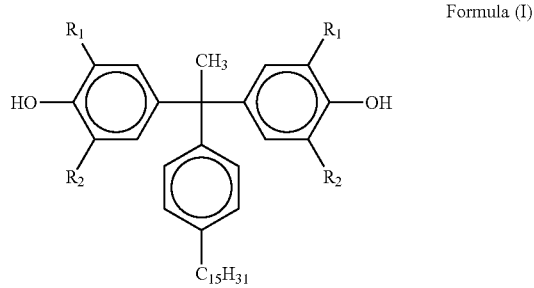

Formula (I)

The present invention also provides a method for the synthesis of a compound of formula I from Cashew Nut Shell Liquid (CNSL), which is a renewable resource material.

BACKGROUND OF THE INVENTION

Cashew nut shell liquid (hereinafter "CNSL") has been known for years to contain compounds useful in various aspects of chemical industry, with particular reference to plastics production. It is of immense interest for various applications. Technical grade CNSL is a commercially available product. CNSL comprises, in major proportion (typically about 80% by weight), a material also sold separately under the trade name CARDANOL™ which is a mixture of the hydroxyalkenylphenols 3-(pentadec-8-ethyl)phenol, 3-(pentadeca-8,11-dienyl)phenol and 3-(pentadeca-8,11,14-trienyl)phenol. Minor constituents include about 18% of a material also sold separately under the trade name CARDOL™, which is a mixture of the 5-substituted resorcinols, and about 2% 2-methylcardol, which is a mixture of the corresponding 2-methyl-5-substituted resorcinols, and other materials that have not been identified.

Bisphenols are known in the art to be useful chemicals. They have been used as difunctional monomers in preparation of various polymers, such as epoxy resins, polyesters, polyethersulfones, polyetherketones, polyetherimides, polyarylates and, in particular, polycarbonates.

It is well known in the art that incorporation of a long alkyl chain in a polymer backbone imparts properties such as increase in the segmental mobility, solubility and hence it improves proccessability of the material. The use of bisphenols having long chain aliphatic substituent as a comonomer is known to offer polymer material with high flow and improved impact resistance. It is therefore of great interest and importance to synthesise new bisphenols with alkyl radical in their structure having the potential of affording polymer material with high proccessability and impact strength. It is of particular interest to develop bisphenols, which may be easily and cheaply obtained from readily available and renewable resource material such as CNSL.

The inventors herein are unaware of any prior art for preparation of the bisphenols of the structure identified above as Formula I.

OBJECTS OF THE INVENTION

The main object of the present invention is to provide a novel bisphenol compound of formula (I).

Another object of the invention is to provide a class of novel bisphenol compounds starting from naturally occurring renewable material; CNSL.

Another object of the invention is to provide a process for the preparation of a novel bisphenol compound of formula (I).

SUMMARY OF THE INVENTION

Accordingly the present invention provides a bisphenol compound of formula (I)

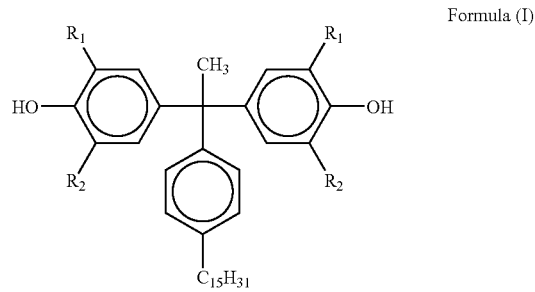

Formula (I)

wherein $R_1$ and $R_2$ are the same or different and are independently either hydrogen or methyl at each occurrence.

In one embodiment, the bisphenol compound is selected from 1,1,1-[bis(4-hydroxyphenyl)-4'-pentadecylphenyl]ethane and 1,1,1-[bis(3-methyl-4-hydroxyphenyl)-4'-pentadecylphenyl]ethane.

The present invention also provides a process for the preparation of a bisphenol compound of formula (I),

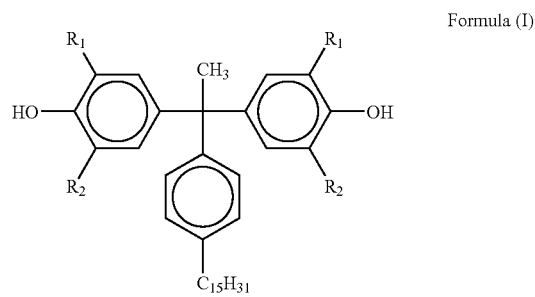

Formula (I)

wherein $R_1$ and $R_2$ are the same or different and are independently either hydrogen or methyl at each occurrence, the process comprising the steps of:

(a) dehydroxylating 3-pentadecyl phenol of formula (II)

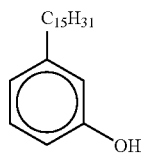

Formula (II)

by reacting the 3-pentadecyl phenol with 1-phenyl-5-chlorotetrazole of formula (III)

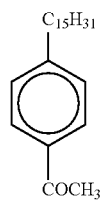

Formula (III)

in presence of a weak base in acetone, refluxing the reaction mixture, removing solvent and pouring the resulting concentrate in water to obtain a precipitate, followed by recrystallization in alcohol to obtain 3-pentadecyl-1-(1-phenyl-tetrazolyloxy)phenyl of formula (IV),

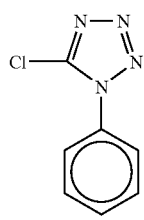

Formula (IV)

(b) hydrogenolysing 3-pentadecyl-1-(1-phenyl-tetrazolyloxy)phenyl of formula (IV), in the presence of about 5% palladium-on-charcoal, in an aromatic hydrocarbon solvent, filtering the reaction mixture and washing insoluble residue with hot alcohol, combining the filtrates, concentrating the combined filtrate by removing the solvent to obtain a sticky residue, extracting residue with toluene and washing it with an aqueous metal hydroxide and then again by water, followed by removal of solvent to obtain pentadecyl benzene of formula (V),

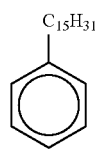

Formula (V)

(c) acetylating the pentadecyl benzene of formula (V) with an acetylating agent, in the presence of a Lewis acid catalyst, in an organic solvent, warming the reaction mixture, pouring the reaction mixture in ice, extracting the resultant compound with a halocarbon solvent, washing extracts so obtained with dilute HCl and then again by water, followed by removal of solvent to obtain 4-acetyl pentadecyl benzene of formula (VI),

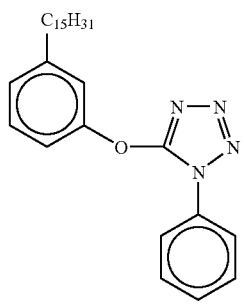

Formula (VI)

(d) reacting 4-acetyl pentadecyl benzene of formula (VI) with substituted or unsubstituted phenol, in the presence of an acidic catalyst, dissolving the reaction mixture in ethyl acetate and subsequently washing with an aqueous solution of a weak base and water, respectively, removing the solvent and purifying the resultant product to obtain the desired bisphenol compound of formula (I).

In one embodiment of the invention the weak base used in step (a) is selected from potassium carbonate and sodium carbonate.

In another embodiment the alcohol used in step (a) is selected from methanol and ethanol.

In another embodiment, the refluxing in step (a) is carried out for a period of at least 16 hours.

In another embodiment the aromatic hydrocarbon solvent used in hydrogenolysis in step (b) is selected from toluene and benzene.

In another embodiment, hydrogenolysing in step (b) is carried out in a Parr reactor.

In another embodiment, step (b) is carried out at a pressure of about 40 psi and at a temperature in the range of 35-40° C. for at least 8 hours.

In another embodiment the acetylating agent used in step (c) is selected from the group consisting of acetic acid, acetic anhydride and acetyl chloride.

In another embodiment the metal hydroxide used is an alkali metal hydroxide selected from sodium hydroxide and potassium hydroxide.

In another embodiment the Lewis acid catalyst used in step (c) is selected from $AlCl_3$ and $BF_3$.

In another embodiment the organic solvent used for acetylation in step (c) is selected from a halogenated hydrocarbon or a nitrogen compound.

In another embodiment the halogenated hydrocarbon solvent is selected from dichloromethane and chloroform.

In another embodiment the nitrogen compound used as an organic solvent is selected from nitro methane and nitro benzene.

In another embodiment, in step (c) acetylation is carried out at a temperature below 5° C., for a period of at least about 2 hours, followed by warming the reaction mixture to a temperature of 30-40° C., for at least 5-6 hours.

In another embodiment the acid catalyst used in phenol condensation in step (d) is selected from the group consisting of acidic clays, sulfated zirconia, 3-mercaptopropionic acid, glacial acetic acid, hydrogen chloride and any mixture thereof.

In another embodiment, in step (d) reaction of 4-acetyl pentadecyl benzene of formula (VI) with substituted or unsubstituted phenol is effected at a temperature in the range of 30-50° C., for a period of about 4 days.

DETAILED DESCRIPTION OF THE INVENTION

The present invention relates to novel bisphenol compounds useful as difunctional monomers for the synthesis of various high performance polymers. The compounds of the invention are preferably synthesized from Cashew Nut Shell Liquid (CNSL), which is a renewable resource material. The bisphenol compounds prepared according to the invention are 1,1,1-[bis(4-hydroxyphenyl)-4'-pentadecylphenyl]ethane and 1,1,1-[bis(3-methyl-4-hydroxyphenyl)-4'-pentadecylphenyl]ethane.

The bisphenol compounds of the present invention are of formula (I),

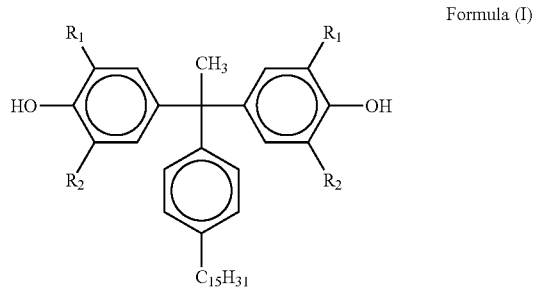

Formula (I)

wherein $R_1$ and $R_2$ are identical or different and independently at each occurrence represent hydrogen or methyl.

Preparation of bisphenol compounds of formula I comprises of three steps, viz., Step A, B and C as shown in Scheme (I) below.

Scheme (I)

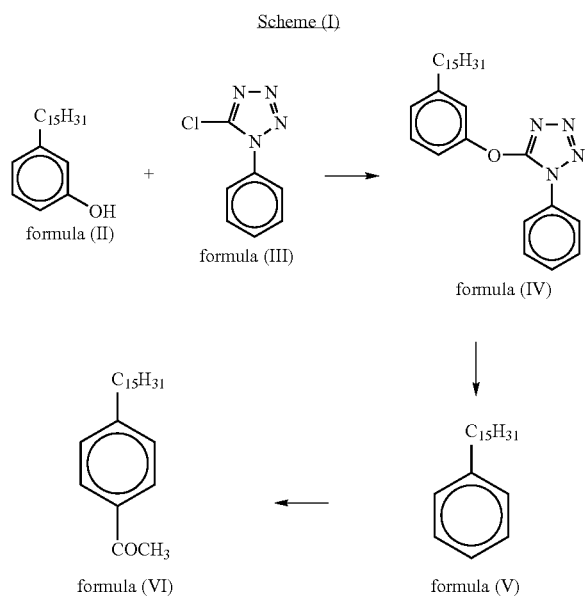

Step A of the method of the invention comprises dehydroxylation of 3-pentadecyl phenol to obtain pentadecyl benzene.

The replacement of phenolic hydroxyl group by hydrogen is an important organic transformation. Several methods are available for dehydroxylation such as, use of: cyclohexene/Pd/C/AlCl$_3$ (Synthesis, 1978, 397), HI/CH$_3$COOH (J. Org. Chem., 1979, 44, 26, 4813), NaBH$_4$/NiCl$_2$ (J. Chem. Soc. Perkin Trans. I, 1992, 1897), 1-phenyl-5-chlorotetrazole/[H]/Pd—C (J. Am. Chem. Soc., 1966, 88, 4271). Phenolic hydroxyl group can be replaced by hydrogen in two steps: conversion of phenol to ether followed by cleavage with an alkali metal in liquid ammonia. (J. Org. Chem., 1973, 38, 13, 2314; J. Org. Chem., 1964, 29, 3124; J. Org. Chem., 1966, 31, 1662), (J. Am. Chem. Soc., 1937, 59, 603; J. Am. Chem. Soc., 1937, 59, 1488; J. Am. Chem. Soc., 1938, 60, 94). A traceless perfluoroalkylsulfonyl (PFS) linker was reported for the deoxygenation of phenols (Org. Lett., 2001, 3, 17, 2769).

In Step A of the process of preparation of pentadecyl benzene, the use is made of 1-phenyl-5-chlorotetrazole for etherification reaction with 3-pentadecyl phenol, followed by catalytic hydrogenolysis being most preferred; among the methods available for dehydroxylation of phenol.

In the present invention, the process for the preparation of 3-pentadecyl-1-(1-phenyl-tetrazolyloxy)phenyl, comprises reaction of 3-pentadecyl phenol with 1-phenyl-5-chlorotetrazole in presence of potassium carbonate as a base and acetone as a solvent, refluxing temperature is necessary in the duration of 16-18 hours for complete etherification reaction. The amount of potassium carbonate is double over stoichiometric amount of substrate.

In catalytic hydrogenolysis step, while subjecting 3-pentadecyl-1-(1-phenyl-tetrazolyloxy)phenyl to hydrogenolysis, the catalyst 5% palladium-on-charcoal is most preferred, with a proportion of 20%-40% by weight, pressure of 40-60 p.s.i., and temperature in the range of 35-40° C. being most preferred.

Step B of the method of the invention comprises acetylation of pentadecyl benzene of formula II with acetyl chloride selectively at para-position using a Lewis acid catalyst., under classical acetylation reaction conditions.

U.S. Pat. No. 4,663,484 describes acetylation of aromatics. Suitable conditions for acetylation are described in J. Am. Chem. Soc. 1999, 121, 2657-2661. Usable examples of acetylating agents can include acetic acid, acetic anhydride and acetyl chloride, with acetyl chloride being particularly preferred. The acetylating agent is preferably used in a proportion from 1 to 1.5 moles per mole of pentadecyl benzene, with 1 to 1.2 moles being more preferred.

The Lewis acid catalysts used in acetylation reaction are generally AlCl$_3$ or BF$_3$. The acetylation reaction in step A may preferably be conducted in a solvent. In general, it is possible to use any one of the solvents, which are typically employed for acetylation of aromatic compounds. Usable examples can include any organic halogen compounds such as dichloromethane, chloroform and nitro compounds such as nitromethane, nitrobenzene. However, use of halocarbon solvents such as dichloromethane, chloroform is preferred. Preferably acetylation reaction is conducted in a nitrogen atmosphere. The reaction can be effected in a temperature range of from 0° C. to 40° C. to attain selectivity and better yield. The yields from this reaction are virtually quantitative and the quality of acetylated 4-pentadecyl benzene is such that it can be directly used for phenol condensation reaction.

Step C of the present invention comprises reacting 4-acetyl pentadecyl benzene, under reaction producing conditions, with a phenolic compound, substituted or unsubstituted one. Such conditions include presence of an acidic catalyst, as illustrated by ion exchange resins in the acid form, acidic clays, sulfated zirconia and excess hydrogen chloride, the later preferably used in combination with a meracaptan such as 3-mercaptopropionic acid. U.S. Pat. No. 6,255,439 describes methods of phenol condensation reaction with carbonyl compound for bisphenol synthesis, the disclosures of which are incorporated by reference herein. For phenol condensation reaction temperatures in the range of about 10° C.-50° C. are typical.

The intermediates and products formed in each step A-B-C can be worked up and isolated by conventional means. These include solvent removal (when solvent is employed), washing, drying and recrystallisation.

The following examples are illustrative of the invention and should not be construed to limit the scope thereof in any manner.

EXAMPLE I

Synthesis of 3-pentadecyl-1-(1-phenyl-tetrazolyloxy)phenyl

A 500-ml., round-bottomed flask fitted with an efficient condenser and a magnetic stirring bar was charged with 3-pentadecyl phenol (25 g, 82 mmol), 1-phenyl-5-chlorotetrazole (14.82 g, 82 mmol), anhydrous potassium carbonate (22.69 g, 164.1 mmol) and 250 ml acetone. The mixture was stirred and heated under reflux for 18 hours. After cooling, the reaction mixture was concentrated; 100 ml water was added and cooled overnight at 5° C. The solid obtained was collected by filtration and dried in air, giving a crude product, which was then dissolved in 100 ml hot methanol. The solution was filtered while hot to remove small amount of insoluble material and cooled in ice, yielding 3-pentadecyl-1-(1-phenyl-tetrazolyloxy)phenyl as a white solid. The yield obtained was 26 g. (70% of the theoretical).

EXAMPLE II

Synthesis of Pentadecyl Benzene

Into a solution of 3-pentadecyl-1-(1-phenyl-tetrazolyloxy) phenyl (20 g, 44.5 mmol) in 200 ml toluene palladium-on-charcoal (4 g, 20% by weight) was added, and the mixture was shaken with hydrogen in a Parr apparatus at 40 p.s.i. and 40° C. for 8 hours. The mixture was filtered, and the insoluble residue was washed with hot ethanol (3×100 ml). The filtrates were combined and concentrated leaving a sticky residue, which was dissolved in 200 ml toluene, shaken with 100 ml of 10% aqueous sodium hydroxide solution, and the layers were separated. The aqueous layer was again extracted with 100 ml toluene. After combining, organic layer was washed with water and dried over sodium sulfate. Removal of toluene yielded crude pentadecyl benzene, which was then purified by column chromatography. Pure pentadecyl benzene was obtained in a yield of 11 g (85% of the theoretical).

EXAMPLE III

Synthesis of 4-acetyl Pentadecyl Benzene

A 500-ml-three-necked round-bottomed flask, with an efficient cooling was charged with aluminium chloride (5.82 g, 43.67 mmol) and dichloromethane (100 ml). Acetyl chloride (3.42 g, 43.67 mmol) was added to the vigorously stirred reaction mixture over a period of 15 minutes. Pentadecyl benzene (10 g, 34.66 mmol) was added over a period of 30 minutes; the clear solution was stirred at 0° C. for 2 hours and allowed to warm to room temperature. The reaction mixture was poured in ice and extracted with dichloromethane (3×100 ml), the combined organic layers was washed with 1 N hydrochloric acid (2×30 ml) and water (3×50 ml), dried over sodium sulfate and the solvent was evaporated to obtain 4-acetyl pentadecyl benzene as a low melting faint yellow solid. The yield was 10 g (87% of theoretical).

EXAMPLE IV

Synthesis of 1,1,1-[bis(4-hydroxyphenyl)-4'-pentadecylphenyl]ethane

A 250-ml-three-necked round-bottomed flask fitted with a magnetic stirrer and gas dip tube was charged with 4-acetyl pentadecyl benzene (5 g, 15.15 mmol), phenol (8.54 g, 90.90 mmol) and 0.13 ml of 3-mercaptopropionic acid. The resulting mixture was stirred at room temperature for 15 minutes, after which anhydrous hydrogen chloride gas was bubbled into the reaction mixture for 4 days at 50° C., whereupon the mixture solidified. The reaction mixture was dissolved in ethyl acetate (500 ml), washed with aqueous sodium bicarbonate (3×100 ml) solution and water (3×100 ml), layers separated and dried over sodium sulfate. Vacuum stripping of solvent afforded a pink solid, which was purified by column chromatography. The desired 1,1,1-[bis(4-hydroxyphenyl)-4'-pentadecylphenyl]ethane was obtained in a yield of 4 g (52% of theoretical).

EXAMPLE V

Synthesis of 1,1,1-[bis(3-methyl-4-hydroxyphenyl)-4'-pentadecylphenyl]ethane

A 250-ml-three-necked round-bottomed flask fitted with a magnetic stirrer and gas dip tube was charged with p-acetyl pentadecyl benzene (5 g, 15.15 mmol), o-cresol (9.83 g, 90.90 mmol) and 0.13 ml of 3-mercaptopropionic acid. The resulting mixture was stirred at room temperature for 15 minutes, after which anhydrous hydrogen chloride gas was passed in to mixture for 4 days at 50° C., whereupon the mixture solidified. The reaction mixture was dissolved in ethyl acetate (500 ml), washed with aqueous sodium bicarbonate (3×100 ml) solution and water (3×100 ml), and dried over sodium sulfate. Vacuum stripping of solvent afforded a pink solid, which was purified with column chromatography. The desired 1,1,1-[bis(3-methyl-4-hydroxyphenyl)-4'-pentadecylphenyl]ethane was obtained in a yield of 4 g (50% of theoretical).

ADVANTAGES OF THE INVENTION

The present invention provides novel bisphenol compounds with alkyl radical in their structure, which has the potential to be utilized as difunctional monomers for the preparation high performance polymers with excellent proccessability by virtue of the presence of pentadecyl chain.

The present invention also provides a simple and economical procedure for the synthesis of novel bisphenol compounds since it uses CNSL as the starting material, which is a naturally occurring and renewable resource material.

It will be apparent to those skilled in the art that various changes and modifications may be made to the disclosure herein without departing from the invention. It is intended that the appended claims cover changes and modifications that fall within the true spirit and scope of the invention.

We claim:

1. A bisphenol compound of formula (I)

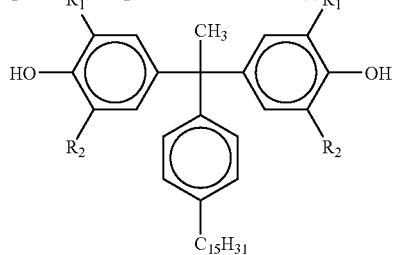

wherein the compound is selected from the group consisting of 1,1,1-[bis(4-hydroxyphenyl)-4'-pentadecylphenyl]ethane and 1,1,1-[bis(3-methyl-4-hydroxyphenyl)-4'-pentadecylphenyl]ethane.

* * * * *

UNITED STATES PATENT AND TRADEMARK OFFICE
CERTIFICATE OF CORRECTION

| | |
|---|---|
| PATENT NO. | : 7,446,234 B2 |
| APPLICATION NO. | : 11/528490 |
| DATED | : November 4, 2008 |
| INVENTOR(S) | : Arvind Sudhakar More and Prakash Purushottam Wadgaonkar |

It is certified that error appears in the above-identified patent and that said Letters Patent is hereby corrected as shown below:

On the title page, item (30) Foreign Application Priority Data
"2000/DEL/2005" should be -- 2600/DEL/2005 .......... 27 September 2005 --.

Signed and Sealed this

Seventeenth Day of March, 2009

JOHN DOLL
*Acting Director of the United States Patent and Trademark Office*